United States Patent [19]

Nakajima et al.

[11] Patent Number: 5,116,949
[45] Date of Patent: May 26, 1992

[54] BENZOYL UREA COMPOUND-ALBUMIN COMPLEX

[75] Inventors: Tsunetaka Nakajima; Tadao Okamoto; Nobuo Kondo; Masahiro Watanabe; Koichi Yamauchi; Kazumasa Yokoyama, all of Hirakata; Takahiro Haga, Kusatsu; Nobutoshi Yamada, Kusatsu; Hideo Sugi, Kusatsu; Toru Koyanagi, Kusatsu, all of Japan

[73] Assignees: Ishihara Sangyo Kaisha Ltd.; The Green Cross Corporation, both of Osaka, Japan

[21] Appl. No.: 400,941

[22] Filed: Aug. 31, 1989

[30] Foreign Application Priority Data

Sep. 12, 1988 [JP] Japan .................. 63-226553

[51] Int. Cl.$^5$ .................. C07K 15/00; C07K 15/12; A61K 37/02
[52] U.S. Cl. .................. 530/363; 530/362
[58] Field of Search .................. 530/362, 363; 514/21

[56] References Cited

U.S. PATENT DOCUMENTS

| | | |
|---|---|---|
| 3,535,423 | 10/1970 | Ordas . |
| 3,920,442 | 11/1975 | Albert et al. . |
| 3,992,553 | 11/1976 | Sirrenberg et al. . |
| 4,083,977 | 4/1978 | Miesel . |
| 4,085,226 | 4/1978 | Sirrenberg et al. . |
| 4,366,155 | 12/1982 | Canada . |
| 4,727,077 | 2/1988 | Haga et al. . |

FOREIGN PATENT DOCUMENTS

| | | |
|---|---|---|
| 164694 | 5/1985 | European Pat. Off. . |
| 0178572 | 4/1986 | European Pat. Off. . |
| 01292263 | 8/1986 | European Pat. Off. . |
| 0233559 | 8/1987 | European Pat. Off. . |
| 58-21612683 | 12/1983 | Japan . |
| 8302230 | 7/1983 | World Int. Prop. O. . |

OTHER PUBLICATIONS

Chemical Abstracts, vol. 98, p. 67, abstr. No. 101190r, Columbus OH, US; & JP-A-57 109 721 (Ishihara Sangyo Kaisha Ltd) Jul. 8, 1982 *Abstract*.
Chemical Abstracts, vol. 100, 1984, p. 356, abstr. No. 109119e, Columbus, OH, US; & JP-A-58 216 126 (Ono Pharmaceutical Co., Ltd) Dec. 15, 1983 *Abstract*.

*Primary Examiner*—Howard E. Schain
*Attorney, Agent, or Firm*—Oblon, Spivak, McClelland, Maier & Neustadt

[57] ABSTRACT

A benzoyl urea compound-albumin complex comprising a benzoyl urea compound of the formula:

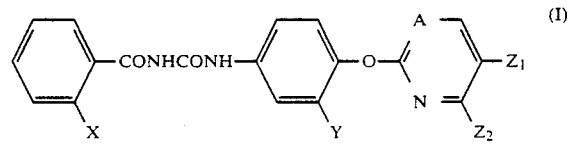

wherein X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom and A is CH or a nitrogen atom, and albumin.

5 Claims, No Drawings

BENZOYL UREA COMPOUND-ALBUMIN COMPLEX

The present invention relates to a benzoyl urea compound-albumin complex.

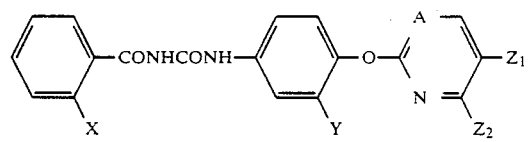

wherein X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom and A is CH or a nitrogen atom, is known to be a compound having excellent antitumor activities (Japanese Unexamined Patent Publications No. 109721/1982, No. 1670/1986 and No. 93163/1986).

This benzoyl urea compound has a characteristic that it is hardly soluble in either water or an organic solvent. As a means for formulating or solubilizing a hardly soluble active ingredient, there may generally be mentioned emulsification by means of a surfactant, encapsulation with e.g. cyclodextrin, conversion to a derivative, ribosome-modification or microcapsulation. However, in the case of the benzoyl urea compound, it has been difficult to prepare a formulation capable of adequately exhibiting the drug activities even when such a means is adopted (Japanese Unexamined Patent Publication No. 27965/1986).

Under these circumstances, the present inventors have conducted various studies for formulating such a benzoyl urea compound and have finally found that when a complex is formed by utilizing the affinity of the benzoyl urea compound with albumin, the stability of the benzoyl urea compound will be excellent, and it will be useful as a medicine and will be capable of being administered by intravenous injection. The present invention has been accomplished on the basis of this discovery.

The present invention provides a benzoyl urea compound-albumin complex comprising a benzoyl urea compound of the formula:

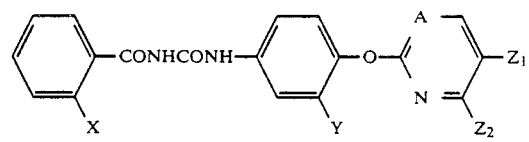

wherein X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom and A is CH or a nitrogen atom, and albumin.

Now, the present invention will be described with reference to the preferred embodiments.

The benzoyl urea compound to be used in the present invention is represented by the above formula I. It includes, for example, compounds of the following formulas:

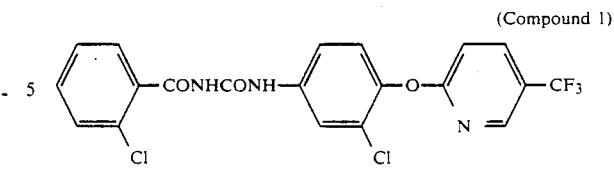

(Compound 1)

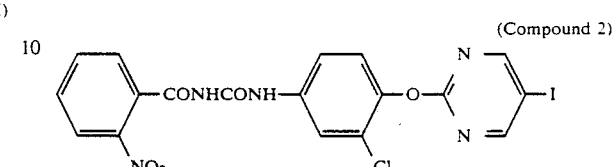

(Compound 2)

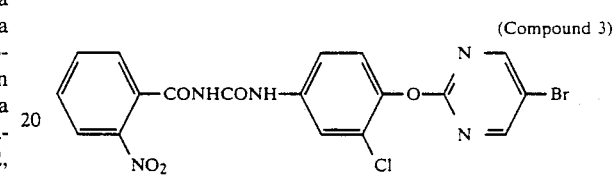

(Compound 3)

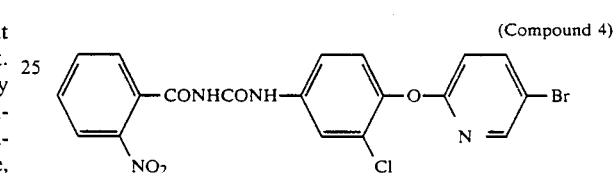

(Compound 4)

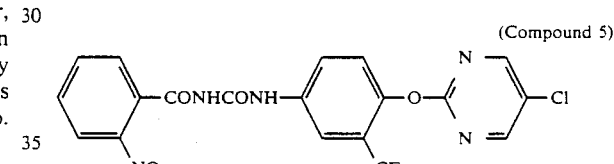

(Compound 5)

and

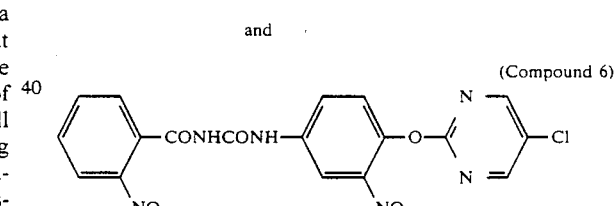

(Compound 6)

The benzouyl urea compounds of the formula I are generally known and can be produced by the process disclosed in e.g. Japanese Unexamined Patent Publication No. 109721/1982 or by a similar process. The albumin to be used in the present invention is preferably an albumin derived from human from the viewpoint of the problem of antigenicity. There is no particular restriction as to the albumin so long as it is purified for pharmaceutical uses. The purity is preferably such that at least 80% as analyzed by electrophoresis is albumin. As a method for obtaining such human-derived albumin, an ethanol fractional method (Japanese Examined Patent Publications No. 2869/1972 and No. 5297/1960) or a method of heating in the presence of an organic acid (Japanese Examined Patent Publications No. 1604/1968 and No. 401321/1976) may be mentioned. Particularly preferred is the one wherein albumin is heat-treated (preferably at 60° C. for about 10 hours) for inactivation treatment of hepatitis virus.

The complex of the present invention may be prepared by a conventional technique. For example, the benzoyl urea compound is dissolved in a suitable organic solvent (for example, DMSO or ethanol) to obtain a solution having a concentration of from 0.01 to 1 W/V%, to which a solution prepared by dissolving albumin in an aqueous solvent at a concentration of from 0.1 to 10 W/V% is mixed in a substantially equal amount (from 0° to 30° C. for from 1 to 24 hours). The mixing ratio is such that the benzoyl compound is in an amount of from 1 to 100 mols per mol of the albumin.

In the complex of the present invention thus obtained, the benzoyl urea compound is in an amount of from 1 to 50 molecules per molecule of the albumin. Further, the two components are not required to be chemically bonded to each other. It is rather preferred that the complexing is made by a hydrogen bond or by an action between the molecules.

The complex obtained by the present invention may be formulated in accordance with conventional methods commonly employed for pharmaceutical products. Further, it may be presented in the form of a dry formulation prepared by freeze-drying a liquid formulation. In this case, a suitable conventional stabilizer may be used depending upon the particular active ingredient or phospholipid. Further, it is effective to incorporate a nonionic surfactant to improve the solubility of the dry formulation. Such a dry formulation is dissolved in or diluted with a physiologically acceptable aqueous solution such as a physiological sodium chloride solution for use. However, it may be formed into tablets, capsules, enteric drugs, suspensions, granules, powders, injection drugs or suppositories by conventional methods for formulation.

The complex obtained by the present invention has a solubility in water improved over the benzoyl urea compound itself, and its activity increases by a few times to a few tens times by the improved solubility. Further, the toxicity is suppressed at a low level as compared with the single administration, and an increase in the effects is expected with an increase of the acceptable dose.

Further, the complex can be formulated into an injection drug, and intravenous administration will be possible, whereby an improvement in the local affinity or quick effects is expected. It is also expected that a side effect to the intestine by the drug upon oral administration is suppressed, and the effects will increase due to an increase in the absorption through the intestine.

Thus, the complex of the present invention makes it possible to effectively formulate a hardly water soluble drug, and it makes a new development possible in the field of the medical industry or the clinical treatment.

Now, the present invention will be described in further detail with reference to Examples and Test Examples. However, it should be understood that the present invention is by no means restricted by such specific Examples.

EXAMPLE 1

The acute toxicity, the dose and the administration method of the complex of the present invention were studied.

Acute toxicity

The complex of the present invention was intravenously administered to $CDF_1$ mice (10 animals) at a dose of 500 mg/kg, whereby none of mice died. Thus, the acute toxicity ($LD_{50}$) of the complex of the present invention was found to be more than 500 mg/kg.

Dose

The dose varies depending upon the diseased condition, the sex, the body weight, the formulation, etc. However, for instance, when the composition of the present invention is intravenously administered against human malignant lymphoma or lung cancer, the benzoyl urea compound of the formula I is administered in a daily dose of from 5 to 100 mg/kg to an adult in one to three times per week.

Method for administration

The complex of the present invention may be formulated as described above and orally, intravenously or through the rectum administered. Among them, intravenous administration is particularly preferred.

TEST EXAMPLE 2

Solubility

By using Compound 3, the solubility of the complex of the present invention in distilled water for injection drug was examined. The results are shown in Table 1.

TABLE 1

|  | Solubility (as Compound 3) |
|---|---|
| Compound 3 | 0.024 μg/ml |
| Compound 3-albumin complex | 4.5 mg/ml |

EXAMPLE 3

Preparation of a complex of a benzoyl urea compound (Compound 3) and human serum albumin 1 g of human serum albumin was extracted with 100 ml of a 5% glacial acetic acid-isooctane solution preliminarily dried over anhydrous sodium sulfate, without shaking at 0° C. for at least 6 hours, and then the extract solution was removed by decantation. This operation of isooctane extraction was repeated two more times, followed by vacuum drying to remove isooctane and glacial acetic acid. The dried human serum albumin was dissolved in purified water and subjected to dialysis in the purified water at 1° C. for 3 days, followed by freeze-drying to obtain human serum albumin containing no fatty acid. This albumin was dissolved in a phosphate buffer solution having a pH of 7.4 and an ion strength of 0.16 to obtain a 1% solution. To 10 ml of this solution, a solution having 14.79 mg of Compound 3 dissolved in 0.2 ml of DMSO, was added and mixed. This mixture was stirred at room temperature for 2 hours and then left to stand at 4° C. for at least 6 hours. The solution thus obtained was subjected to dialysis in a phosphate buffer solution having a pH of 7.4 and an ion strength of 0.16 at 1° C. for 2 days to remove free Compound 3 and DMSO. The solution of the complex thus obtained was subjected to dialysis in a 0.5% sodium chloride-1% glucose solution at 1° C. for 2 days for stabilization. The solution thus obtained was freeze-dried to obtain the desired complex. The constituting proportion of the complex was 20 molecules of the benzoyl urea compound (Compound 3) per molecule of the albumin.

What is claimed is:

1. A benzoyl urea compound-albumin complex comprising a benzoyl urea compound of the formula:

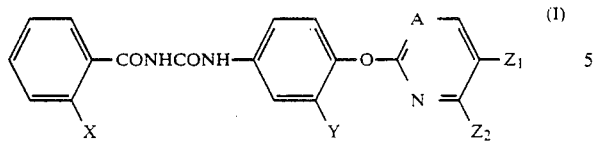

wherein X is a halogen atom or a nitro group, Y is a hydrogen atom, a halogen atom, a nitro group or a trifluoromethyl group, $Z_1$ is a halogen atom or a trifluoromethyl group, $Z_2$ is a hydrogen atom or a halogen atom and A is CH or a nitrogen atom, and albumin.

2. The complex according to claim 1, wherein the benzoyl urea compound is in an amount of from 1 to 100 mols per mol of the albumin.

3. The complex according to claim 1, wherein the benzoyl urea compound is in an amount of from 1 to 50 molecules per molecule of the albumin.

4. The complex according to claim 1, wherein the benzoyl urea compound is selected from the group consisting of:

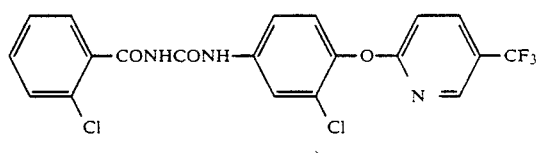

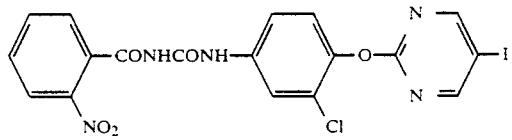

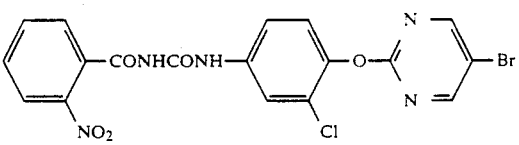

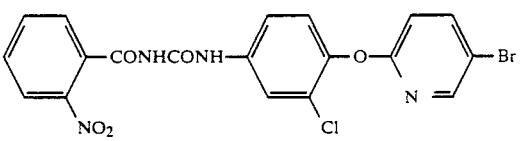

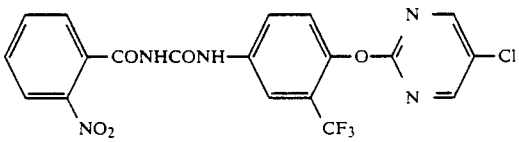

and

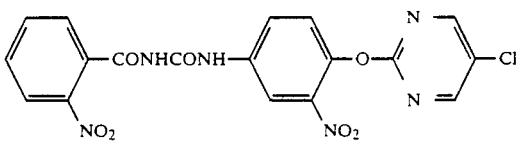

5. The complex according to claim 1, wherein the albumin is albumin derived from human.

* * * * *